United States Patent
Whitehurst et al.

(10) Patent No.: US 7,110,823 B2
(45) Date of Patent: Sep. 19, 2006

(54) RF TELEMETRY LINK FOR ESTABLISHMENT AND MAINTENANCE OF COMMUNICATIONS WITH AN IMPLANTABLE DEVICE

(75) Inventors: Todd K Whitehurst, Frazier Park, CA (US); Kelly H McClure, Simi Valley, CA (US); Salomo S Murtonen, San Gabriel, CA (US)

(73) Assignee: Advanced Bionics Corporation, Valencia, CA (US)

( * ) Notice: Subject to any disclaimer, the term of this patent is extended or adjusted under 35 U.S.C. 154(b) by 522 days.

(21) Appl. No.: 10/447,336

(22) Filed: May 29, 2003

(65) Prior Publication Data

US 2003/0229383 A1    Dec. 11, 2003

Related U.S. Application Data

(60) Provisional application No. 60/388,127, filed on Jun. 11, 2002.

(51) Int. Cl.
*A61N 1/00* (2006.01)
(52) U.S. Cl. ............................... 607/60; 607/32
(58) Field of Classification Search ............... 607/16, 607/30–32, 60; 128/903
See application file for complete search history.

(56) References Cited

U.S. PATENT DOCUMENTS

| | | | |
|---|---|---|---|
| 4,532,932 A | 8/1985 | Batty, Jr. | |
| 4,586,508 A | 5/1986 | Batina et al. | |
| 5,342,408 A * | 8/1994 | deCoriolis et al. | 607/32 |
| 5,800,473 A | 9/1998 | Faisandier | |
| 6,024,539 A | 2/2000 | Blomquist | |
| 6,045,513 A | 4/2000 | Stone et al. | |
| 6,053,887 A | 4/2000 | Levitas et al. | |
| 6,106,551 A | 8/2000 | Crossett et al. | |
| 6,115,636 A | 9/2000 | Ryan | |
| 6,135,949 A | 10/2000 | Russo et al. | |
| 6,208,894 B1 | 3/2001 | Schulman et al. | |
| 6,315,721 B1 | 11/2001 | Schulman et al. | |
| 6,472,991 B1 | 10/2002 | Schulman et al. | |
| 2001/0053926 A1 | 12/2001 | Whitehurst | |
| 2003/0114898 A1 * | 6/2003 | Von Arx et al. | 607/60 |
| 2003/0149459 A1 * | 8/2003 | Von Arx et al. | 607/60 |
| 2003/0187484 A1 * | 10/2003 | Davis et al. | 607/60 |

* cited by examiner

*Primary Examiner*—Robert Pezzuto
*Assistant Examiner*—Yun Haeng Lee
(74) *Attorney, Agent, or Firm*—Bryant R. Gold; Victoria A. Poissant

(57) ABSTRACT

Communication between an implantable device(s), such as a neural stimulator, and an external remote device(s), e.g., a computer in a clinician's office, a computer in a patient's home, or a handheld patient remote control, is performed entirely via an RF link. In order to conserve power, the RF telemetry system of the implant is only activated periodically; with the period of activation being sufficiently short so as to allow a reasonably prompt response of the implant to a request for a communication session by the external device. In order to assure reliable communication, the RF information may be encoded, as appropriate, with error correction codes.

20 Claims, 5 Drawing Sheets

DETECT MODE

RECEIVE MODE

FULL DATA TRANSFER (XFER) MODE

RF TELEMETRY LINK FOR ESTABLISHMENT AND MAINTENANCE OF COMMUNICATIONS WITH AN IMPLANTABLE DEVICE

The present application claims the benefit of U.S. Provisional Application Ser. No. 60/388,127, filed Jun. 11, 2002, which application is incorporated herein by reference in its entirety.

BACKGROUND OF THE INVENTION

The present invention relates to controlling an implantable device, e.g., an implantable medical device, and more particularly to using an RF telemetry link to establish and maintain communications with the implantable device.

Due to a multitude of advances in electronics, packaging, sensors, pumps, and pharmacology, implantable devices such as stimulators, pumps, and sensors are becoming increasingly more complex. However, communication with implants has not advanced significantly over the past decade.

Conventional implantable devices (e.g., pacemakers) implement a relatively simple form of establishment and maintenance of communication with external devices. Some devices contain a magnetic sensor, and a communication session is established when an external permanent magnet is brought into close proximity (e.g., within a few centimeters), triggering the magnetic sensor. The magnetic sensor may also be used for communication, e.g., the presence of a permanent magnet for a certain period of time may adjust a parameter or toggle the state of activation of the implantable device. Such a system of establishing and maintaining communication may be triggered erroneously by a strong magnetic field in the environment. Also, the complexity and speed of communication is inherently limited.

Other devices communicate via an inductive link. In these systems, a communication session may be established when an external coil is energized, producing a strong magnetic field, and is then brought into close proximity with an implanted coil contained within or next to the implant. This system has the advantage that the implantable device may be a passive receiver, i.e., the energy received in its coil may provide all of the energy required for causing activation of the implant and initiating a communication session. This allows the implant to expend virtually no energy in its receiver outside of communication sessions. However, such a system also has disadvantages. The inductive magnetic fields decrease rapidly with distance, and thus the external device must be in close proximity to the implant (e.g., within a few centimeters). Also, since the energy to activate the implant may be provided by the external device, the external device requires a relatively sizeable source of power. Such a strong magnetic field may also be difficult to modulate efficiently, and this may lead to either an increased power expenditure or a relatively low limit on communication bandwidth.

Conventional implant systems generally operate in a relatively open-loop fashion. That is, the patient implanted with the device has little or no control over the implant. The patient also has no computer or other automated system that assists in monitoring and/or programming the implanted device. However, implanted systems of increased complexity typically require an increased amount of monitoring and programming by an external user and/or an automated system. Communication to support such increased amount of monitoring and programming must be done more frequently.

By way of example, an implant patient may need to adjust the programmed settings of an implantable stimulator several times throughout the day, or an automated system may adjust the implant every few minutes when it is within communication range.

Complex implantable devices also typically require the exchange of a larger amount of data with an external user and/or an automated system than has heretofore been achievable. For example, an external user may want to frequently sample the readings of a number of implanted sensors as well as the current programmed settings, or an automated system may upload a significant volume of data as a time series of sensor readings. Additionally, rapidly changing signals such as an ECG, EEG, EMG, or ENG require high communication data rates in order to be communicated to an external device in a reasonable period of time.

Representative communication and/or control links with implantable medical devices are as described in the following U.S. Pat. No. 5,800,473: Systems, methods, and apparatus for automatic updating of a programmer for an active implantable medical device; U.S. Pat. No. 4,586,508: Implant communication system with patient coil; U.S. Pat. No. 4,532,932: Implant communication system with frequency shift means; U.S. Pat. No. 6,135,949: Apparatus for monitoring and/or controlling a medical device; U.S. Pat. No. 6,115,636: Telemetry for implantable devices using the body as an antenna; U.S. Pat. No. 6,106,551: Communication method for implantable medical device; U.S. Pat. No. 6,053,887: Medical treatment apparatus and method; U.S. Pat. No. 6,045,513: Implantable medical device for tracking patient functional status; and U.S. Pat. No. 6,024,539: Systems and methods for communicating with ambulatory medical devices such as drug delivery devices. All of these prior art approaches suffer from one or more deficiencies.

It is thus evident that there is a need in the art for an improved communication and control link with an implantable device, particularly implantable medical devices that are more complex and sophisticated than prior art implantable devices.

SUMMARY OF THE INVENTION

The present invention addresses the above and other needs by providing a means for establishing and maintaining communication between an implantable device(s) and an external remote device(s), e.g., a computer in a clinician's office, a computer in a patient's home, or a handheld patient remote control. The establishment of communication between the implant device and the external device is performed entirely via an RF link. In order to conserve power, the RF telemetry system of the implant is only activated periodically; with the period of activation being sufficiently short so as to allow a reasonably prompt response of the implant to a request for a communication session by the external device. In order to assure reliable communication, the RF information may be encoded, as appropriate, with error correction codes.

It is to be noted that for purposes of the present application, any of the terms "implantable", "implanted", or "implant" may be used to refer to a device, e.g., the "implant device" or the "implanted unit", or to a component or element, e.g., the "implant receiver" or the "implantable antenna", that is implanted or that is intended to be implanted.

It is a feature of the invention to provide an RF telemetry link between an external device and an implant device that allows the system comprising the external device and implant device to operate efficiently, e.g., at low power consumption, and effectively, e.g., reliably and without error.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
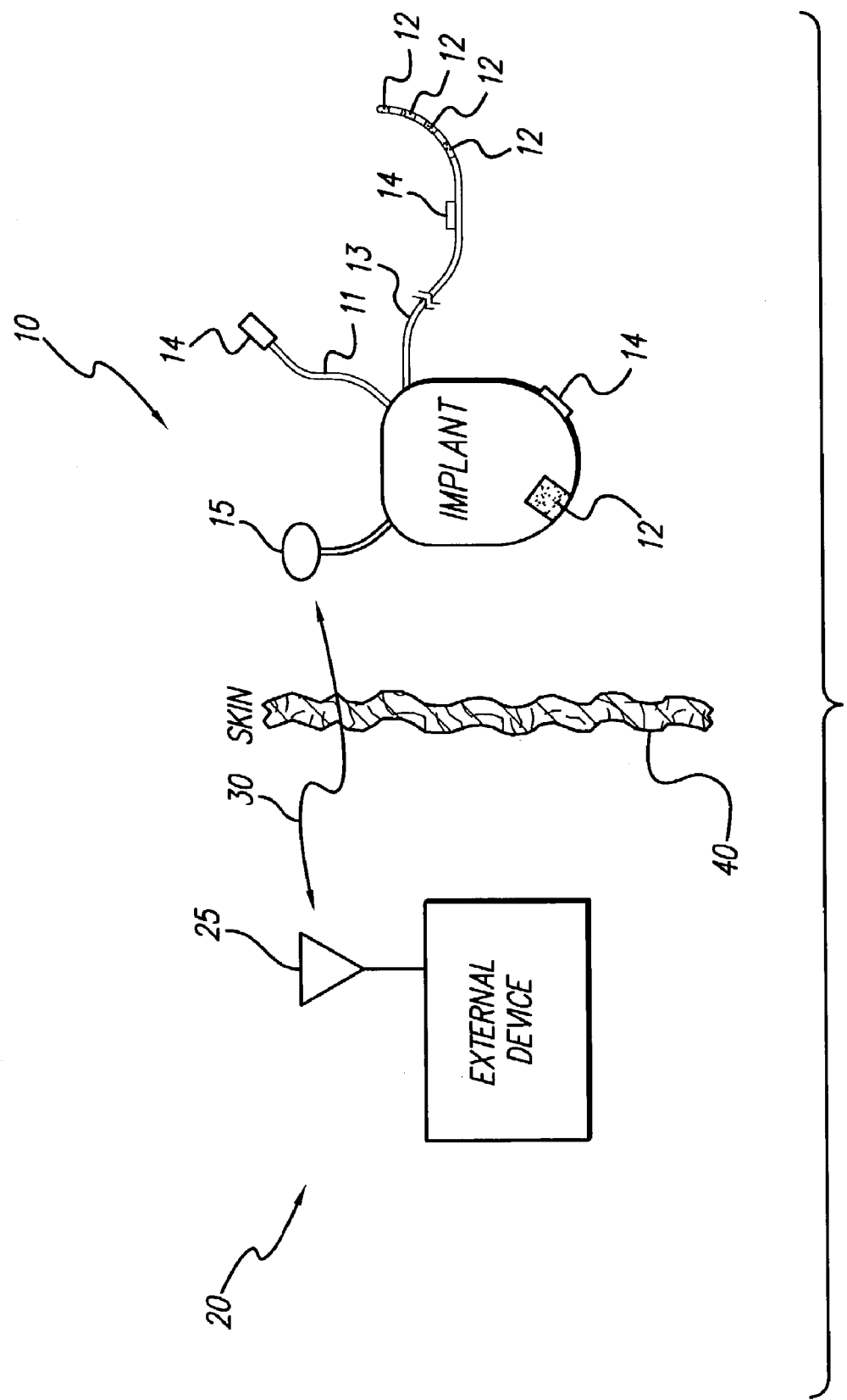
FIG. 1 depicts an external device and an implantable device having an RF Telemetry Link established therebetween.

With reference to FIG. 1, the present invention provides a way for the establishment and maintenance of a pure RF telemetry-based communication system between an implanted device(s) 10 and an external device(s) 20. The external device 20 includes a suitable antenna 25 through which transmitted radio frequency (RF) signals may be sent to the implant device 10, and through which RF signals transmitted from the implant device 10 may be received. Similarly, the implant device 10 includes an antenna 15 for receiving the RF signals transmitted by the external device, and through which RF signals may be transmitted to the external device. Thus, an RF telemetry link, represented as the wavy arrow 30 in FIG. 1, is established between the implant device 10 and the external device 20. It is to be understood that, as appropriate, the external antenna 25, and/or the implanted antenna 15, may actually comprise two separate antennas, one for receiving RF signals and one for transmitting RF signals.

The implanted device(s) 10, including its antenna 15, is typically implanted under the skin 40 of a patient in a suitable location, as is known in the art. The implanted device 10 may comprise a neurostimulator, a muscle stimulator, or any other type of electrical or magnetic stimulation device. As such, the implantable device 10 typically includes one or more electrodes 12 on a lead 13 through which electrical stimulation pulses may be applied or other electrical activity associated with body tissue may be sensed. One or more electrodes 12 may also be incorporated into the case of the implant device 10. The implanted device(s) 10 may also include a pump(s) for the infusion of medication and other substances through a catheter 11.

The implanted device(s) 10, in addition to providing electrical or fluid stimulation as described above, or in lieu thereof, may include one or more sensor(s) 14 for the detection of levels of various substances, e.g., medications, hormones, neurotransmitters, electrolytes, enzymes, gases, glucose, etc., in various body spaces. Such detected substances may include, e.g., plasma, cerebrospinal fluid, lymph, peritoneum, fluids in the pleural space, etc. As seen in FIG. 1, such sensors 14 may be positioned at various locations, e.g., on the lead 14, on the catheter 14, or as part of or attached to the case of the implant device 10. Alternatively, the sensors 14 may be coupled to the implant device 10 through a dedicated lead or other coupling link.

The implanted device(s) 10 may additionally include an internal sensor(s) for the measurement of various parameters of relevance to the implant(s), the patient, or the physician. Such parameters may include, e.g., pressure, acceleration, voltage, impedance, other physiological parameters associated with the patient, and the like.

The implanted antenna 15 may be internal to the implanted device 10, mounted on the case of the implanted device 10, or simply attached through wires to the implanted device 10. In some embodiments, the implanted antenna 15 may be incorporated into the lead 13, or the catheter 11, or into a non-hermetically-sealed header associated with the case of the implant 10.

RF telemetry systems are capable of achieving communication over remote distances and at high data rates. However, these systems require a significant amount of power in order to operate continuously. This power demand is prohibitive to an implanted device. The present invention is directed to an implantable device that includes an RF telemetry system as its primary means of communication, e.g., a system that communicates in the 402–405 MHz frequency range. The RF telemetry system provided by the invention may also implement an inductive communication system and/or may also include a magnetic sensor for the establishment and maintenance of communication, as is known in the art, but these inductive or magnetic systems are not considered primary.

Hence, in accordance with the present invention, the establishment of communication between an implant device 10 and an external device 20 is performed entirely via an RF link 30. However, in order to conserve power, the RF telemetry system of the implant is only activated periodically; as explained more fully below, with the period of activation being sufficiently short so as to allow a reasonably prompt response of the implant to a request for a communication session by the external device.

Figure 2:
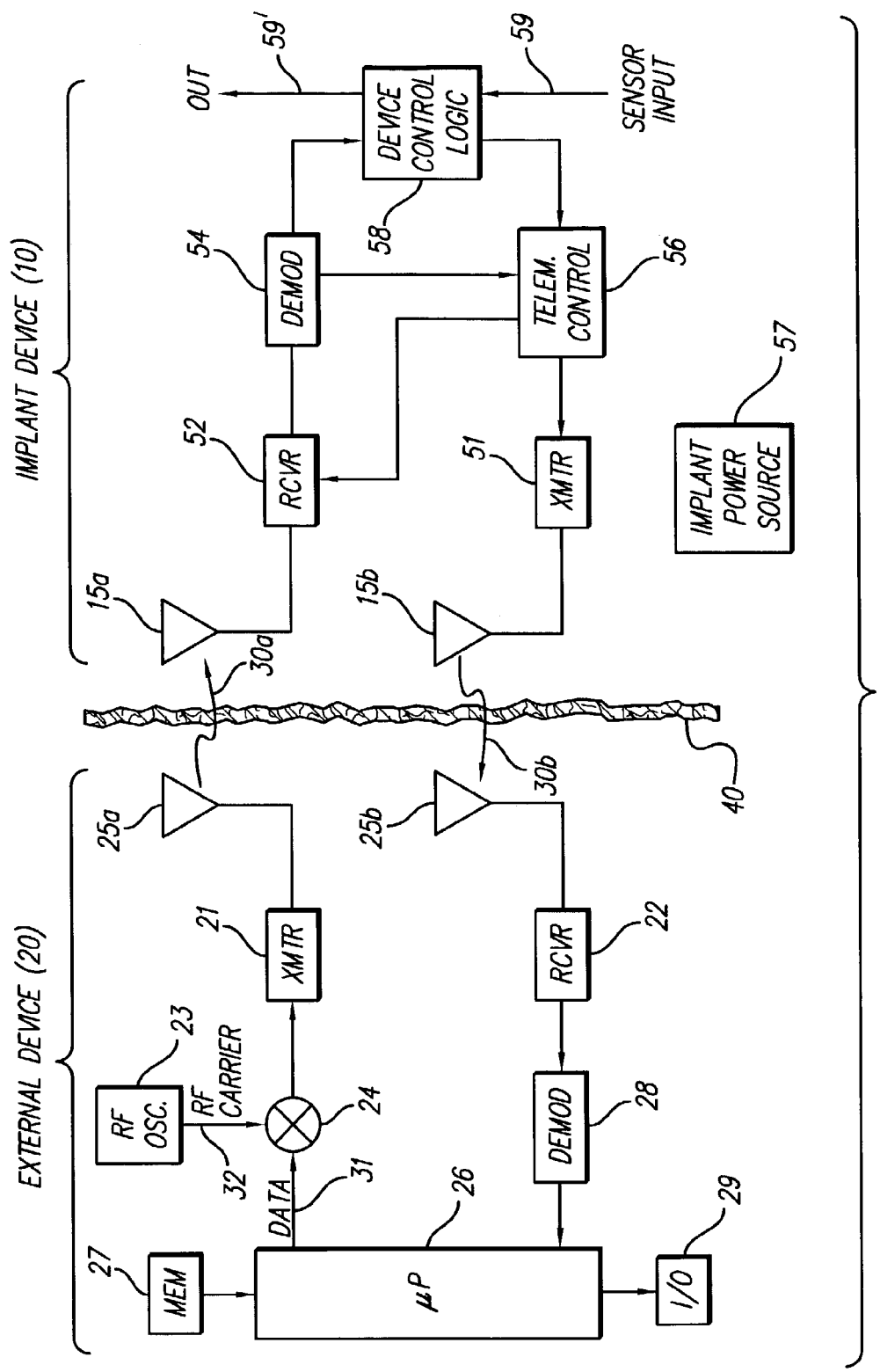
FIG. 2 shows a functional block diagram of the receiver and transmitter portions of an external device and an implantable device.

As seen in FIG. 2, the external device 20 includes a transmitter 21, and means for generating an RF signal to be transmitted, e.g., an RF oscillator 23, a mixer (or modulator) 24, and a data source 26. The data source 26, in many embodiments of external devices 20, comprises a microprocessor (μP) coupled to suitable memory circuitry 27 and input/output (I/O) devices 29, as is known in the art. The I/O devices 29 may include lights, displays, speakers, and other indicators, as well as keys, buttons, and other switches, as needed. The microprocessor 26 may be replaced by state logic circuits, or other control circuits, as needed or desired for a particular application.

In operation, the microprocessor 26, or equivalent circuitry, provides a data stream 31 that modulates an RF carrier signal 32, generated by the RF Oscillator 23. The resulting modulated RF signal is applied to the transmitter 21 and broadcast from the antenna 25a as RF signal 30a. When the data stream 31 is absent, then an unmodulated RF carrier signal is transmitted. Such unmodulated RF carrier signal may be used, in accordance with one embodiment of the invention, as explained more fully below, to alert the implant device 10 that a communication cycle is desired.

The RF signal 30a, whether modulated or unmodulated, may be received through implanted antenna 15a and receiver (RCVR) circuit 52 providing the RCVR 52 is enabled (turned ON). However, a key feature of the present invention, as explained more fully below, is that the implant receiver 52 is only turned ON at certain times as controlled by a telemetry control circuit 56. When turned ON, the implant receiver 52 receives the RF signal 30a and applies it to a demodulator circuit 54. The demodulator circuit 54 detects the data, if any, that is embedded in the RF signal, and sends the detected data to implant device control logic 58. Device control logic 58 may comprise a microprocessor, state control logic, or other control circuitry, depending upon the particular application. The device control logic 58 is preferably programmable, meaning that such control logic 58 may be configured for different applications as controlled by appropriate programming data signals that are received by the control logic 58.

Still with reference to FIG. 2, the device control logic 58 instructs telemetry control logic 56 in an appropriate manner so that the receiver circuit 52 is ON or OFF, and so that a transmitter 51 is ON or OFF, as appropriate. If the transmitter 51 is ON, appropriate data is transmitted by the transmitter 51, as RF signal 30b, as received from the device control logic 58, through antenna 15b to the external device 20. Although not shown in FIG. 2, it is to be understood that the transmitter 51 of the implant device 10 includes a suitable RF oscillator and modulator (mixer) circuitry, or equivalent circuitry, so that the transmitted RF carrier signal 30b may be generated.

The device control logic 58, e.g., a microprocessor circuit or equivalent, generates appropriate output signals on signal line(s) 59' that allow the implant device 10 to perform its intended function, e.g., to generate output stimulus pulses on selected electrodes, or to sense certain physiological parameters through selected sensors. The signals sensed by the sensors 14 are applied to the device control logic 58 over sensor input line(s) 59. These sensor signals are then processed by the device control logic 58, in an appropriate manner, and converted to sensor data signals that may be used to help control the operation of the implant device 10 and/or transmitted to the external device 20 through the telemetry control circuits 56, transmitter circuit 51 and antenna 15b.

The RF signal 30b, transmitted from the implant device, is received through antenna 25b and receiver circuit 22. The RF signal is then demodulated by demodulator 28 to recover the data therefrom, and the data is presented to processor 26. Typically, such data is stored in memory circuitry 27 for subsequent downloading and analysis. Alternatively, or conjunctively, such data may be monitored in real time and used to provide operating data to the patient or a clinician regarding the implant device.

Still with reference to FIG. 2, and more particularly with reference to the Implant Device 10 portion of FIG. 2, it is noted that a microprocessor may be used as the device control logic 58, and depending upon the capability of the microprocessor, the function of the telemetry control circuit 56 may be performed by the microprocessor. That is, in some embodiments of the invention, the device control logic 58 and the telemetry control circuit 56 may be realized using a single microprocessor circuit.

It should also be noted that in many embodiments of the invention, the implantable antenna 15a that receives the RF signals 30a from the external device 20, and the implantable antenna 15b that transmits RF signals 30b to the external device 20, may be combined into a single antenna. Similarly, the external antenna 25b that receives the RF signals 30b from the implant device 10, and the external antenna 25a that transmits RF signals 30a to the implant device 10, may be combined into a single antenna.

According to one aspect of the invention, the implanted device 10 periodically, e.g., once per second, activates its RF telemetry receiver 52. If an external transmission is detected, then the RF telemetry receiver 52 remains active, and the RF telemetry transmitter 51 may also be activated. If no external transmission is detected, then the RF telemetry receiver 52 is deactivated (turned OFF) until the next listening period. The RF telemetry receiver 52 of the implanted device is thus constantly going through a "sleep-listen" cycle, as controlled by the telemetry control circuits 56, when no signal is detected.

Figure 3A:
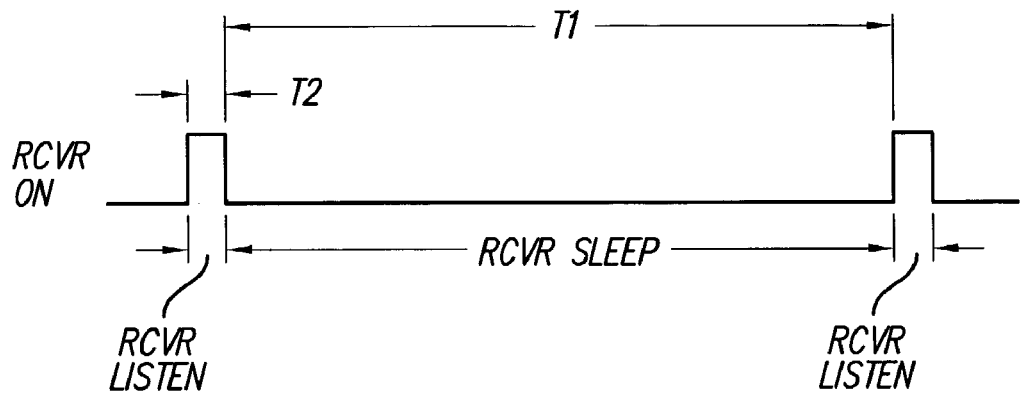
FIGS. 3A, 3B and 3C are timing diagrams that illustrate various modes of operation of the implant receiver in accordance with the invention.

The sleep-listen cycle of the RF telemetry receiver 52 is illustrated in FIG. 3A as a receiver detect mode of operation. In such mode of operation, the receiver 52 is only ON for a very short period of time, T2, relative to the time the receiver 52 is OFF, T1. The OFF time T1 may be between about 1 and 5 seconds, e.g., 1 second, whereas the ON time T2, for this mode of operation, may be a very small fraction of T1, between about 10 and 200 milliseconds, e.g., 20 milliseconds.

When a communication session is to be initiated, the external device 20 (e.g., a patient programmer) activates the external RF transmitter 21 and signals the implant through transmission of an RF signal 30a that it wishes to establish a communication session. To make certain that the implant 10 detects the signal 30a, the external device 20 transmits the signal 30a for a period of time that exceeds the implant receiver 52 OFF time, T1. In this way, the initiate-a-communication-session signal 30a will be assured of being present during at least one of the "listen" portions T2 of the implant receiver 52. Once the implant telemetry receiver 52 detects such a signal, the communication session is allowed to proceed.

The initiate-a-communication-session RF telemetry signal 30a transmitted from the external device to the implant device to initiate a communication session may be a simple signal with no data, e.g., a constant RF carrier signal. Alternatively, the RF telemetry signal transmitted by the external device to the implant to initiate a communication session may carry data, e.g., an attention signal, a constant header, the address of the implant, or the like.

Figure 3B:
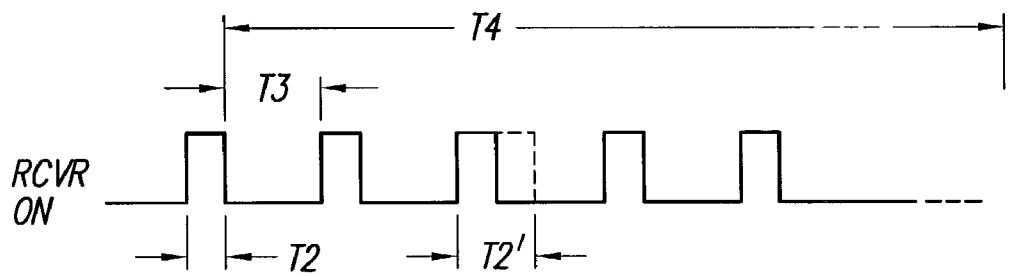

According to another aspect of the invention, once the implantable device detects that a RF telemetry signal has been transmitted by the external device for the purpose of initiating a communication session, the implantable device then enters a more rapid "sleep-listen" cycle, illustrated in FIG. 3B as a "receive mode". During the receive mode, the implant receiver 52 may listen once every 0.1 seconds (that is, T3 is equal to 100 milliseconds). In this more rapid sleep-listen cycle, the implant is looking for the transmission of a separate information packet by the external device 20 that is distinct from the initial activation signal. This new transmission of separate information packet may contain information such as the address or identification code of the implant 10, programming commands, device parameters and status, and/or sensor data. The implant 10 remains in the more rapid "sleep-listen" cycle, or the "receive mode", until after a certain time period has passed after the reception of the last command, e.g., it may have a 10-second timeout. Alternatively, the external device may signal the end of a communication session, which then ends the rapid "sleep-listen" cycle. When the rapid "sleep-listen" cycle ends, the implant resumes the normal "sleep-listen" cycle, i.e., the receiver detect mode (illustrated in FIG. 3A).

According to a further embodiment of the invention, once the implantable device detects the RF telemetry signal transmitted by the external device to initiate a communication session, the implantable device responds with an RF telemetry transmission that indicates to the external device that the implant has received the request for initiation of a communication session and is ready to receive further data and/or commands, i.e., the implant may acknowledge transmissions received from the external device. The external device may then transmit data and/or commands in a long, uninterrupted sequence, referred to as a "full data transfer (XFER) mode" in FIG. 3C. At the conclusion of the full data transfer mode, i.e., after all the data and/or commands have been sent, the implant 10 may send a final acknowledge signal and then may return to the detect mode, or normal "sleep-listen" cycle, illustrated in FIG. 3A.

Figure 3C:

FIG. 3C illustrates a full data transfer mode. In such mode, the implant receiver 52 is turned ON and remains ON until all the needed data has been transferred. During this full data transfer mode, the implant transmitter 51 may likewise be turned ON so that appropriate acknowledgment signals, or other status data, may be sent to the external device 20.

In order for multiple implants to remain separate and distinguishable, each implant 10 is programmed with an address or other means of identification. Commands and requests sent from the external device 20 may include the specific address of a particular implant, and implants that do not match the address ignore the commands. Alternatively, some commands may include a universal address, or no address, and thus may be executed by all implants. As another alternative, implants may receive conditional commands, i.e., commands that are only executed if a certain parameter(s) is within a certain range(s). The parameter(s) and range(s) may be preprogrammed or may be sent as part of the RF telemetry transmission by the external device.

A transmission from the external device 20 typically includes a request by the external device for a specific data transmission to be made from the implantable device 10. In response to such a request, the implantable device 10 may transmit such data, if available, or may transmit an error code if such data is not available.

As is known, a remote and/or high-speed RF telemetry link may suffer from the presence of noise mixed with the signal. In order to minimize the probability of spurious or erroneous transmissions, the implantable device 10 includes a means for detection and/or correction of errors on a received RF telemetry signal(s). The external device 20 preferably includes a means for detection and/or correction of errors on a received RF telemetry signal(s).

A communication session includes the exchange of all telemetry messages between the implant 10 and the external device 20. Such telemetry messages may include programming commands sent by the external device 20 to program the implant 10, or vice versa. Such telemetry messages may also include information on current or past programmed settings of the implant or of the external device. The telemetry messages may further include information relative to the status of the implant or of the external device, e.g., battery voltage. The telemetry messages may additionally include data gathered via sensors 14 carried by, or coupled to, the implant or on (or coupled to) the external device 20, e.g., impedance, heart rate, oxygen level, or the like.

During the beginning of a "listen" period, the RF telemetry receiver 52 of the implanted device 10 is initially placed in a relatively low-power "warm-up" mode, e.g., to allow a frequency reference such as a crystal to become stable. This mode allows the RF telemetry receiver to warm up while minimizing power consumption.

If the implantable device 10 detects that its power source is below a certain threshold, it may discontinue the normal "sleep-listen" cycle and may completely deactivate the RF telemetry system. For example, if the battery voltage of an implant drops below a certain level, it may discontinue RF communication. As a safety measure, the implanted device may also discontinue its functions if the voltage is too low, e.g., it may halt stimulation and/or infusion. An external device that is attempting to communicate with the implant will inform the user that the implant power may be too low for communication if it is unsuccessful in establishing a communication session. The implantable device enters its normal "sleep-listen" cycle when power is restored, e.g., when the battery is recharged above a certain threshold.

Figures 1, 4:
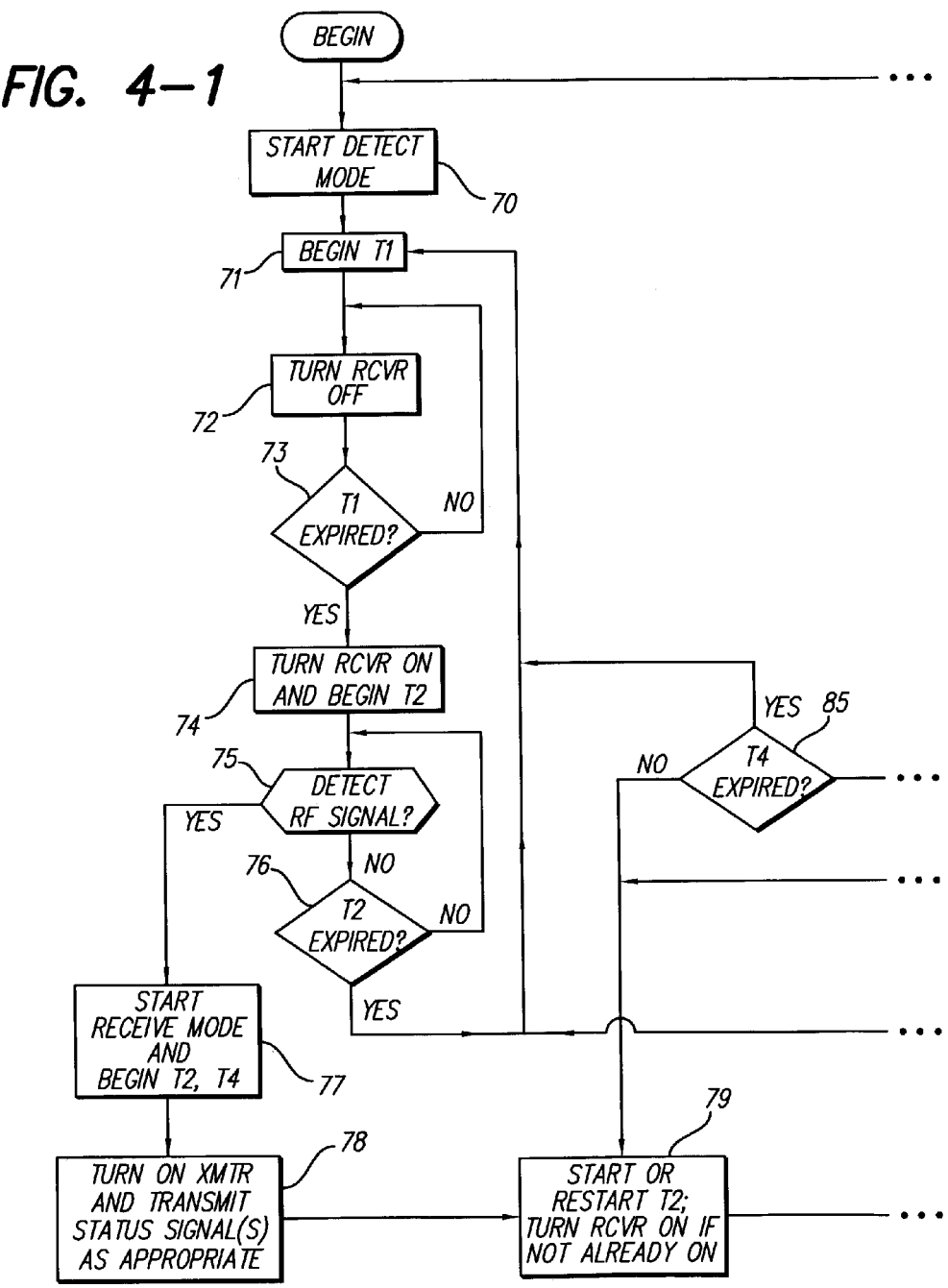
FIG. 4 is a flow chart that illustrates operation of the receiver and transmitter portions of the implant in accordance with one embodiment of the invention. (Note, due to space limitations, FIG. 4 is presented as two figures, labeled as FIG. 4-1 and FIG. 4-2. These two figures are intended to be placed side-by-side, with FIG. 4-1 being on the left and FIG. 4-2 on the right.)
Figures 2, 4:
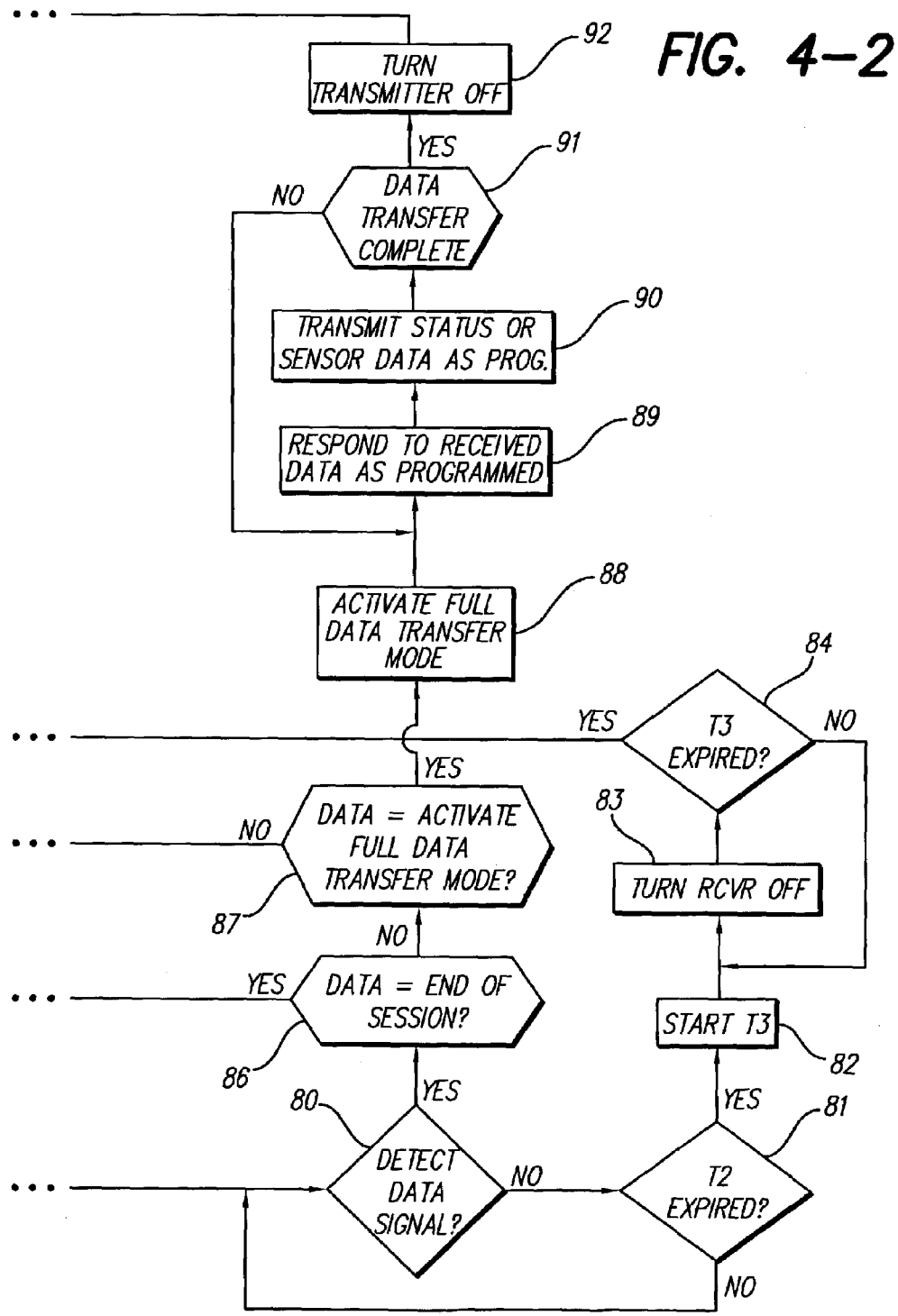

Turning next to FIG. 4 (which, due to space limitations, is presented as two figures, FIG. 4-1 and 4-2, which should be viewed side-by-side, with FIG. 4-1 on the left, and FIG. 4-2 on the right), a flow chart is illustrated that shows one way in which the invention may be practiced. It should be emphasized that the particular details regarding how the invention is practiced will be determined by the specific control logic and circuitry included in the device control logic 58 and/or the telemetry control unit 56 (FIG. 2). This circuitry, in turn, may be operated as controlled by firmware and/or software. The flow chart shown in FIG. 4 thus illustrates just one of several ways that the invention may be operated. Those of skill in the art will be able, given the descriptions presented herein, to fashion numerous ways to achieve the features and objects of the invention, i.e., to establish an RF telemetry link between an external device and implant device that allows for efficient and effective operation of the system.

Each main step or event associated with the process illustrated in FIG. 4 is referred to as a "block". Such blocks are used only for illustrative purposes—to show a particular function that is being carried out—and are not intended to be limiting.

As seen in the example of FIG. 4, and also with reference to FIGS. 3A, 3B and 3C, the system begins by starting the Detect Mode (block 70 and FIG. 3A). This mode turns the Receiver ON and OFF in accordance with a pattern as illustrated in FIG. 3A. That is, an OFF time (or "sleep" time) period T1 is started (block 71 in FIG. 4), during which time the implant receiver 52 is disabled or turned OFF (block 72). Such time period T1 is typically carried out by counting down or counting up a register at a specified clock speed. When the time period T1 has expired (block 73), the receiver 52 is turned ON and a new time T2, much shorter than the time T1, is started (block 74). The time T1, for example, may be on the order of 1–5 seconds, whereas the time T2 may be on the order of 20 to 200 milliseconds.

If an RF signal is detected as being present during time T2 (block 75), i.e., if an external device transmits an RF signal during time T2, then the Receive Mode ("listen" mode) begins (block 77 and FIG. 3B). If an RF signal is not detected during time T2, then the sleep cycle begins again by starting to time out the period T1 (block 71) and by turning OFF the receiver 72 (block 72).

When an RF signal is detected during the time period T2, the receive (or listen) mode begins (block 77). At the beginning of the receive mode, the time period T2 begins, as does a time out period T4. Also, during the receive mode, the transmitter 51 may be turned ON, and a status signal(s) may be transmitted back to the external device 20, e.g., to notify the external device that the RF signal was received, as appropriate (block 78). During the time period T2, the receiver 52 remains ON (or is turned ON if it was not ON previously) and a determination is made as to whether a data signal is present within the RF signal that is detected (block 80). In one embodiment, shown in FIG. 4, the time period T2 may be restarted (block 79). If the time period T2 times out (i.e., expires) without a data signal being detected (YES branch of block 81), then a new OFF-time period T3 is started (block 82) during which time period T3 the receiver is turned OFF (block 83). As suggested in FIG. 3B, the time period T3 is less than the time period T1 (FIG. 3A). By way of example, the time period T3 may be on the order to 50–200 milliseconds. Thus, it is seen that the receive mode (FIG. 3B) operates much the same as the detect mode (FIG. 3A) except that the receiver-off time (or "sleep" time) T3 during the receive mode is much shorter than the receiver-off time T1 during the detect mode.

When the sleep time T3 expires (YES branch of block 84), then a determination is made as to whether the receive mode time out period T4 has expired (block 85). If so, the system reverts to the detect mode (blocks 71–76) during which mode a slow sleep-listen pattern begins (T1 sleep; T2 listen). If not, the receive mode pattern continues (blocks 79–84) during which a faster sleep-listen pattern is maintained (T3 sleep; T2 listen).

Should a data signal, e.g., a command, programming, address, or end-of-session signal, be detected during the receive mode's listening period T2 (YES branch of block 80), then the type of data received is ascertained and acted upon in an appropriate manner. For example, if the received data indicates the end of a communication session (YES branch of block 86), then the receive mode ends, and the detect mode (blocks 71–76) begins. If the received data indicates that a full data transfer mode is to begin (YES branch of block 87), then a full data transfer mode is activated (block 88 and FIG. 3C).

During the full data transfer mode, the receiver 52 and transmitter 51 are turned ON and remain ON until turned OFF. The received data is processed and acted upon, as programmed (block 89), and data available within the implant device, e.g., status data or sensor data, is transmitted to the external device as programmed (block 90). If the data transfer is complete (YES branch of block 91), i.e., if all the data being sent to the implant receiver 52 has been received, and if all the data to be transmitted to the external device through the transmitter 51 has been sent, then the transmitter is turned OFF (block 92) and the detect mode begins (block 70). If the data transfer is not complete (NO branch of block 91), then the implant device continues to process and act upon the received data as programmed (block 89) and to transmit sensor or status data available within the implant device to the external device (block 90).

If the received data during the receive mode (FIG. 3B) indicates that something other than a full data transfer mode is to begin (NO branch of block 87), then the time period T2 is restarted and the receiver is turned ON, or remains ON (block 79), thereby effectively extending the listen time period T2. An extended time period T2 is illustrated in FIG. 3B as the time period T2'. The listen (or receive) time period T2 can be extended in this manner for so long as the data detected indicates that the data being received does not indicate an end of session or a full data transfer is to occur. Such an extended receive time period may be used, for example, when a relatively long sequence of data is being sent to the implant without the need to activate the full data transfer mode (i.e., without the need to turn the transmitter ON).

Additional applications of the invention include communication between two or more implanted devices. According to one embodiment of the invention, an implantable device may operate independently. According to another embodiment of the invention, an implantable device may operate in a coordinated manner with other implantable devices, or other devices external to the patient's body. For example, a series of stimulating devices may be implanted adjacent to a number of related sites to allow a means of multi-electrode stimulation. As another example, a series of sensing devices may be implanted in different areas to sense differences in compounds in different regions of the body. Information sensed by one or more devices may be used to control the stimulation and/or infusion parameters of the sensing devices as well as other devices in a closed loop manner. According to another embodiment of the invention, the sensing and stimulating means are both incorporated into a single implant. According to yet another embodiment of the invention, the stimulation and/or infusion means are incorporated into at least one implant (that may or may not have sensing means), and the stimulation and/or infusion may ultimately be controlled by at least one other device having sensing means.

While the invention herein disclosed has been described by means of specific embodiments and applications thereof, numerous modifications and variations could be made thereto by those skilled in the art without departing from the scope of the invention set forth in the claims.

What is claimed is:

1. A medical system comprising:
an external device having means for generating and transmitting an RF signal; and
an implantable device, the implantable device comprising
an implantable antenna,
an implantable receiver coupled to the implantable antenna, said implantable receiver being adapted to receive the RF signal,
means for controlling the implantable receiver so that the implantable receiver operates in one of a detect mode, a receive mode, or a full data transfer mode, and
means for controlling the implantable device in response to data and commands contained within the received RF signal,
wherein during the detect mode the implantable receiver is OFF for a time period T1 and ON for a time period T2, where T2 is much shorter than T1, and
wherein during the receive mode the implantable receiver is OFF for a time period T3 and ON for a time period T2, where T2 is less than T3, and T3 is less than T1, and
wherein during the full data transfer mode the receiver is ON all the time;
whereby an RF telemetry link is established between the external device and the implantable device through which RF signals may be sent to the implantable device from the external device.

2. The medical system of claim 1 wherein the external device further includes a receiver for receiving an RF signal and wherein the implantable device further includes a transmitter coupled to an implantable antenna through which RF signals may be transmitted, whereby RF signals may be sent from the implantable device to the external device.

3. The medical system of claim 2 wherein the time period T1 comprises a time period of about 1 to 5 seconds.

4. The medical system of claim 3 wherein the time period T2 comprises a time period of about 10 to 200 milliseconds.

5. The medical system of claim 1 wherein the receive mode has a maximum time out period T4 that limits the amount of time during which the receive mode may be activated, where T4 is much greater than T3.

6. The medical system of claim 1 wherein the time period T2 may be extended during the receive mode.

7. A medical system comprising:
an external device having means for generating and transmitting an RF signal; and
an implantable device, the implantable device having
an implantable antenna,
an implantable receiver coupled to the implantable antenna, said implantable receiver being adapted to receive the RF signal transmitted by the external device, and
means for controlling the implantable receiver so that it operates in one of a detect mode or a receive mode,
wherein during the detect mode the implantable receiver is OFF for a time period T1 and ON for a time period T2, where T2 is much shorter than T1, and wherein during the receive mode the implantable receiver is OFF for a time period T3 and ON for a time period T2, where T2 is less than T3, and T3 is less than T1,
whereby an RF telemetry link is established between the external device and the implantable device through which RF signals may be sent to the implantable device from the external device during the time period T2.

8. An implantable medical device comprising:
an implantable antenna,
an implantable receiver coupled to the implantable antenna, said implantable receiver being adapted to receive an externally-generated RF signal,
means for controlling the implantable device in response to data and commands contained within the received RF signal,
means for controlling the implantable receiver so that it operates in one of a detect mode or a receive mode,
wherein during the detect mode the implantable receiver is OFF for a time period T1 and ON for a time period T2, where T2 is much shorter than T1, and wherein during the receive mode the implantable receiver is OFF for a time period T3 and ON for a time period T2, where T2 is less than T3, and T3 is less than T1.

9. The implantable medical device of claim 8 wherein the implantable device further includes a transmitter and a transmit antenna, and wherein the transmitter is coupled to the transmit antenna and provides a communications path through which RF signals may be sent from the implantable device to an external device.

10. The implantable medical device of claim 8 wherein the time period T1 ranges between about 1 to 5 seconds.

11. The implantable medical device of claim 10 wherein the time period T2 ranges between about 10 and 200 milliseconds.

12. The implantable medical device of claim 8 wherein the receive mode has a maximum time out period T4 that limits the amount of time during which the receive mode may be activated, where T4 is much greater than T3.

13. The implantable medical device of claim 8 wherein the time period T2 may be extended during the receive mode.

14. The implantable medical device of claim 8 wherein the means for controlling the implantable receiver comprises means for controlling the implantable receiver so that the implantable receiver operates in one of a detect mode, a receive mode, or a full data transfer mode.

15. A method for establishing and maintaining an RF communications link between an external device and an implantable device, the external device having means for generating and transmitting an RF signal; the implantable device having an implantable antenna coupled to an implantable receiver; the method comprising steps for:
initiating a detect mode within the implantable device wherein the implantable receiver is sequentially turned OFF and ON, wherein during the detect mode the ON time of the implantable receiver is much shorter than the OFF time of the implantable receiver;
initiating a receive mode within the implantable device whenever an RF signal is detected during the ON time of the implantable receiver, wherein during the receive mode the implantable receiver is sequentially turned OFF and ON, wherein the OFF time of the implantable receiver during the receive mode is much shorter than the OFF time of the implantable receiver during the detect mode; and
sending RF communication signals to the implantable device during the ON time of the implantable receiver.

16. The method of claim 15 further including maintaining the receive mode ON until after a prescribed timeout period has passed after the reception of a last RF communication signal, and then turning the receive mode OFF and turning the detect mode ON after the prescribed timeout period has elapsed without reception of an RF communication signal.

17. The method of claim 16 wherein the prescribed timeout period comprises at least 10 seconds.

18. The method of claim 15 further including maintaining the receive mode ON until a command is received through the RF communication signal that the receive mode is to be terminated, and then turning the receive mode OFF and turning the detect mode ON upon receipt of such command.

19. The method of claim 15 further including
initiating a full data transfer mode whenever control data contained within an RF communication signal received from the external device indicates the full data transfer mode is to be turned ON;
turning the full data transfer mode OFF whenever control data contained within an RF communication signal received from the external device indicates the full data transfer mode is to be turned OFF;
wherein during the full data transfer mode the implantable receiver remains ON continuously.

20. The method of claim 15 further including
initiating a full data transfer mode whenever control data contained within an RF communication signal received from the external device indicates the full data transfer mode is to be turned ON;
turning the full data transfer mode OFF after the full data transfer mode has remained ON for a prescribed timeout period;
wherein during the full data transfer mode the implantable receiver remains ON continuously.

* * * * *